(12) United States Patent
Wegerer (10) Patent No.: US 7,687,674 B2
(45) Date of Patent: Mar. 30, 2010

(54) LOW TEMPERATURE PROCESS FOR RECOVERING AND PRODUCING PARA-XYLENE AND HEAT EXCHANGE NETWORK THEREFORE

(75) Inventor: David A. Wegerer, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 735 days.

(21) Appl. No.: 11/617,387

(22) Filed: Dec. 28, 2006

(65) Prior Publication Data
US 2008/0161626 A1    Jul. 3, 2008

(51) Int. Cl.
C07C 5/27    (2006.01)
(52) U.S. Cl. .................. 585/477; 585/478; 585/910
(58) Field of Classification Search .......... 585/477, 585/478, 910
See application file for complete search history.

(56) References Cited

U.S. PATENT DOCUMENTS

| | | | |
|---|---|---|---|
| 3,996,305 A | 12/1976 | Berger | |
| 4,246,073 A | 1/1981 | Umeda et al. | |
| 4,466,202 A | 8/1984 | Merten | |
| 4,584,423 A | 4/1986 | Nacamuli et al. | |
| 4,586,986 A | 5/1986 | Preusser et al. | |
| 4,642,406 A | 2/1987 | Schmidt | |
| 4,670,618 A | 6/1987 | Bellinger | |
| 4,899,012 A | 2/1990 | Sachtler et al. | |
| 4,899,017 A | 2/1990 | Yan | |
| 4,973,764 A | 11/1990 | Oswald et al. | |
| 5,191,152 A | 3/1993 | Forte | |
| 5,336,840 A | 8/1994 | Forte | |
| 5,417,844 A | 5/1995 | Boitiaux et al. | |
| 5,476,823 A | 12/1995 | Beck et al. | |
| 5,658,453 A | 8/1997 | Russ et al. | |
| 5,665,223 A | 9/1997 | Bogdan | |
| 5,723,710 A | 3/1998 | Gajda et al. | |
| 5,759,236 A | 6/1998 | Bruck | |
| 5,763,720 A | 6/1998 | Buchanan et al. | |
| 5,811,629 A | 9/1998 | Hubbell et al. | |
| 5,847,256 A | 12/1998 | Ichioka et al. | |
| 5,866,740 A | 2/1999 | Mikitenko et al. | |
| 5,877,374 A | 3/1999 | Nacamuli et al. | |
| 6,004,452 A | 12/1999 | Ash et al. | |
| 6,051,744 A | 4/2000 | Nacamuli et al. | |
| 6,060,634 A | 5/2000 | Mikitenko et al. | |
| 6,147,272 A | 11/2000 | Mikitenko et al. | |
| 6,376,733 B1 | 4/2002 | Ferraro et al. | |
| 6,565,653 B2 | 5/2003 | Wilsak | |
| 6,573,418 B2 | 6/2003 | Miller et al. | |
| 6,600,083 B2 | 7/2003 | Doyle et al. | |
| 6,627,783 B2 | 9/2003 | Doyle et al. | |

(Continued)

OTHER PUBLICATIONS

Handbook of Petroleum Refining Processes, 2d. Edition in 1997 by McGraw-Hill.

*Primary Examiner*—Thuan Dinh Dang
(74) *Attorney, Agent, or Firm*—David J Piasecki (57) ABSTRACT

Recent experimental work with currently available adsorbents indicates that operating the adsorption section at lower temperatures improves the para-xylene productivity. As a result, an aromatics complex and heat recovery network for a low temperature adsorptive separation-isomerization loop is disclosed resulting in adsorbents savings in combination with higher capacity thereby enabling smaller adsorbents chambers, a smaller total heat exchanger area and a lower heat exchanger shell count.

20 Claims, 8 Drawing Sheets

U.S. PATENT DOCUMENTS 6,689,929 B2 2/2004 Williams et al.
6,740,788 B1 5/2004 Maher et al.
6,878,855 B2 4/2005 Deckman et al.
2004/0060810 A1 4/2004 Asano et al.
2004/0220439 A1 11/2004 Williams et al.
2005/0228206 A1 10/2005 Amelse
2006/0153755 A1 7/2006 Obuchi et al.

FIG. 1

(PRIOR ART)

LOW TEMPERATURE PROCESS FOR RECOVERING AND PRODUCING PARA-XYLENE AND HEAT EXCHANGE NETWORK THEREFORE

BACKGROUND

1. Technical Field

Processes for recovering and/or producing para-xylene from reformate splitter bottoms and toluene column bottoms are disclosed. More specifically, low temperature processes for recovering and/or producing para-xylene from reformate splitter bottoms and toluene column bottoms are disclosed and heat exchanger networks for the low temperature processes are also disclosed.

2. Description of the Related Art

The xylene isomers, meta-xylene, ortho-xylene and, in particular, para-xylene, are important chemical intermediates. Ortho-xylene is oxidized to make phthalic anhydride which is used to make phthalate based plasticizers among other things. Meta-xylene is oxidized to make isophthalic acid which is used in unsaturated polyester resins.

However, para-xylene has by far the largest market of the three isomers. The largest use of para-xylene is in its oxidation to make terephthalic acid. Terephthalic acid, in turn, is used to make polymers such as polytrimethyleneterephthalate, polybutyleneterephthalate (PBT), and polyethyleneterephthalate (PET). PET is made via condensation polymerization of terephthalic acid with ethylene glycol.

PET is one of the largest volume polymers in the world. It is used to make PET plastics, e.g., two liter beverage bottles. PET is also used to make polyester fiber which, in turn, is used to make clothes and other fabrics Polyester fiber is used both as a homofiber, as well as a blended fiber, such as a blend with cotton. Given the large market for PET plastics and fibers, there is a substantial demand for high purity para-xylene. Further, the demand for para-xylene is several times larger than the demand for ortho and meta-xylene. The demand for para-xylene is also larger than the amount of para-xylene in the xylenes recovered as a by-product from reformate processes, such as the xylenes recovered from catalytic reformers and from pygas (i.e., high temperature clacking to make light olefins). Because the demand for para-xylene is so much larger than the demand for the other xylene isomers and is larger even than the supply of para-xylene in xylenes recovered as a by-product of other processes, it has been found that isomerization of xylene isomers is desirable to increase the amount of para-xylene production.

Para-xylene is typically produced by reforming or aromatizing a naphtha feed in a reformer, for example, a continuous catalytic reformer, and then separating by distillation a $C_8$ aromatics rich fraction from the reformer effluent. The $C_8$ fraction includes neat equilibrium amounts of ethylbenzene and the three xylene isomers, namely, para-, meta- and ortho-xylene. The para-xylene in this $C_8$ aromatics fraction can then be separated using an adsorption process such as a simulated moving bed (SMB) adsorption process Downstream of an adsorption unit, the para-xylene depleted $C_8$ aromatics stream is typically further processed by passing it over a xylene isomerization catalyst in a xylenes isomerization unit. The resulting $C_8$ aromatics stream, now with an approximately equilibrium concentration of xylenes, i.e., a higher concentration of para-xylene (~22 wt %), is recycled to the para-xylene separation process. Thus, the adsorption and isomerization processes are typically employed together; in a loop The xylene isomerization unit can serve at least two functions. First, it re-equilibrates the xylenes portion of the stream, bringing the para-xylene concentration up to the equilibrium concentration of 22 wt %. Thus, in effect, it is creating para-xylene from the other xylene isomers. Second, combination of ethylbenzene isomerization catalyst and ethylbenzene dealkylation catalyst in the isomerization process converts ethylbenzene into additional mixed xylenes as well as converts ethylbenzene to a benzene co-product. Since ethylbenzene boils in the same range as the xylene isomers, it is not economic to recover/remove the ethylbenzene by distillation, hence it is included in the $C_8$ aromatics fraction that is fed to the para-xylene SMB adsorption process. It is highly desirable to remove as much ethylbenzene as possible pet pass so that it does not accumulate in the recycle loop.

Thus, a critical function of the isomerization unit is to convert the ethylbenzene to xylene isomers and benzene by either isomerization and dealkylation, or other means for removing ethylbenzene, depending upon on the type of isomerization process employed. This function is critical because the boiling points of the four $C_8$ aromatics at issue fall within a very narrow 8° C. range, from about 136° C. to about 144° C. (see Table I).

TABLE I

| $C_8$ Compound | Boiling Point (° C.) | Freezing Point (° C.) |
|---|---|---|
| ethylbenzene | 136 | −95 |
| para-xylene | 138 | 13 |
| meta-xylene | 139 | −48 |
| ortho-xylene | 144 | −25 |

As shown above, the boiling points of para-xylene and ethylbenzene are about 2° C. apart. The boiling points of para-xylene and meta-xylene are only about 1° C. apart. As a result, fractional distillation would be impractical is it would require large equipment, significant energy consumption, and/or substantial recycles to provide effective and satisfactory xylene separations.

In processing reformate to extract and then a separate para-xylene product stream, the reformate is first subjected to a separation to remove $C_7$ and lighter material and then fractionated to form a $C_8$ aromatic concentrated material, or xylene enriched stream, which will also include ethylbenzene. This stream is then subjected to an adsorption process to produce an essentially pure para-xylene product, after the desorbent is extracted and toluene removed by fractionation. As noted above, the raffinate from the adsorption process is isomerized to produce para-xylene from the $C_8$ isomers in the raffinate and the product of isomerization is recycled to the adsorption process for removing the newly formed para-xylene. Usually the isomerized raffinate is fractionated before it is recycled to the initial fractionation process upstream of the adsorption unit.

Currently, the adsorption process for separating para-xylene from the other xylene isomers and ethylbenzene is carried out at a temperature of about 177° C. (350° F.). Recent experimental work indicates that operating the adsorption section at a lower temperature improves the SMB adsorption unit productivity Specifically, for a constant cycle time, adsorbent capacity increases as the adsorption temperature decreases. Thus, new processes are required to accommodate modifications of the operating temperature adsorption processes

SUMMARY OF THE DISCLOSURE

In satisfaction of the need for a low adsorption temperature operation, novel heat exchange networks integrating xylene fractionation, adsorption separation, and isomerization units are provided that enable the modification of adsorption temperature to increase or optimize capacity and/or provide a savings in connection with other parameters such as adsorbent amount, utilities consumed, heat exchanger area and shell count.

One disclosed process for producing para-xylene from a feed stream comprising a mixture of $C_8$ aromatic isomers and heavies comprises: introducing a feed stream to a xylene fractionation zone to produce a xylenes enriched stream; cooling the xylenes enriched stream by transferring heat from the xylenes enriched stream to one or more of (i) a first raffinate stream and (ii) an isomerization reactor product stream; introducing the xylenes enriched stream and a desorbent stream to a para-xylene separation zone and producing a first para-xylene enriched stream and the first raffinate stream from the xylenes enriched stream and desorbent stream; heating the first para-xylene enriched stream by transferring heat from the desorbent stream to the first para-xylene enriched stream and feeding the heated first para-xylene enriched stream into a para-xylene distillation zone to produce a second para-xylene enriched stream and part of the desorbent stream; introducing the first raffinate stream to a raffinate column to produce another part of the desorbent stream and a second raffinate stream; heating the second raffinate stream by transferring heat from the isomerization reactor product stream to the second raffinate stream and feeding the heated second raffinate stream into an isomerization zone that converts the second raffinate stream to the isomerization reactor product stream; heating at least a portion of the isomerization reactor product stream by transferring heat from one or more of a para-xylene product stream, the xylenes enriched stream and the desorbent stream, to the isomerization reactor product stream; heating the second para-xylene enriched stream by transferring heat from the para-xylene product stream to the second para-xylene enriched stream; feeding the second para-xylene enriched stream to a finishing column to produce the para-xylene product stream. It will be noted that the order of the above process parts or steps is not relevant unless indicated by the particular process part or step.

In a refinement, the process further comprises introducing the isomerization reactor product stream to a deheptanizer column to produce a light overhead stream and a second feed stream and, feeding the second feed stream to the xylene separation zone with the feed stream.

In another refinement, the process further comprises combining part of the desorbent stream from the raffinate column and part of the desorbent stream from the para-xylene distillation zone to produce the desorbent stream, resulting in a heating of the isomerization reactor product stream prior to being fed to the deheptanizer column by transferring heat to the isomerization reactor product stream from the desorbent stream.

In another refinement, the isomerization reactor product stream is also heated by transferring heat from the para-xylene product stream and the xylenes enriched stream to the isomerization reactor product stream.

In another refinement, the transfer of heat from the xylenes enriched stream to the first raffinate stream is carried out in a first heat exchanger.

In another refinement, the transfer of heat from the xylenes enriched stream to the deheptanizer stream is carried out in a second heat exchanger.

In another refinement, the transfer of heat from the desorbent stream to the first para-xylene enriched stream is carried out in a third heat exchanger.

In another refinement, the transfer heat from the isomerization reactor product stream to the second raffinate stream is carried out in a fourth heat exchanger.

In another refinement, the heating of the isomerization reactor product stream by transferring heat from the para-xylene product stream to the isomerization reactor product stream is carried out in a fifth heat exchanger.

In another refinement, the heating of the isomerization reactor product stream by transferring heat from the desorbent stream to the isomerization reactor product stream is carried out in a sixth heat exchanger.

In another refinement, the heating of the second para-xylene enriched stream by transferring heat from the para-xylene product stream to the second para-xylene enriched stream is carried out in a seventh heat exchanger.

In another refinement, the xylenes enriched stream is cooled to a temperature ranging from about 121° C. to about 204° C. prior to being introduced to the para-xylene separation zone.

In another refinement, the feed comprises a reformate splitter bottoms stream.

In yet another refinement, the feed comprises a combination of a reformate splitter bottoms stream and a toluene column bottoms stream. In a related refinement, the reformate splitter bottoms stream and toluene column bottoms stream have each been passed through a clay treater prior to being introduced to the xylene fractionation zone.

In a refinement, the process further comprises passing the second raffinate stream through a heater prior to feeding the second raffinate stream to an isomerization reactor that converts the second raffinate stream to the isomerization reactor product stream. In a related refinement, the process further comprises passing the isomerization reactor product stream through a cooler prior to feeding the isomerization reactor product stream to an effluent separator that produces an effluent recycle stream and a deheptanizer feed stream.

Another disclosed process for producing para-xylene from a feed stream comprising a mixture of $C_8$ aromatic isomers and heavies comprises: introducing a first feed stream to a xylene fractionation zone to produce a xylenes enriched stream; cooling the xylenes enriched stream to a temperature of between about 155° C. and about 182° C. in a first heat exchanger by transferring heat from the xylenes enriched stream to a raffinate stream and further cooling the xylenes enriched stream in a second heat exchanger by transferring heat from the xylenes enriched stream to a cooled isomerization reactor product stream; feeding the xylenes enriched stream and a desorbent stream to a para-xylene separation zone to produce a first para-xylene enriched stream and the raffinate stream from the xylenes enriched stream and desorbent stream; heating the first para-xylene enriched stream in a third heat exchanger by transferring heat from the desorbent stream to the first para-xylene enriched stream and feeding the heated first para-xylene enriched stream to a para-xylene distillation column to produce a second para-xylene enriched stream; heating the raffinate stream in a fourth heat exchanger by transferring heat from an isomerization effluent stream to the raffinate stream and feeding the heated raffinate stream to an isomerization reactor that converts the raffinate stream to the isomerization reactor product stream; cooling the isomerization reactor product stream in the fourth heat exchanger before heating at least a portion of the isomerization reactor product stream in a fifth heat exchanger by transferring heat from a para-xylene product stream to the isomerization reactor product stream, further heating at least a portion of the isomerization reactor product stream in the second heat exchanger by transferring heat from the xylenes enriched stream to the isomerization reactor product stream and still further heating at least a portion of the isomerization reactor product stream in a sixth heat exchanger by transferring heat from the desorbent stream to the isomerization reactor product stream; heating the second para-xylene enriched stream in a seventh heat exchanger by transferring heat from the para-xylene product stream to the second para-xylene enriched stream; and feeding the second para-xylene enriched stream to a finishing column to produce the para-xylene product stream.

In a refinement, the xylenes enriched stream is cooled to a temperature ranging from about 150° C. to about 170° C. prior to being fed to the para-xylene separation zone.

Yet another disclosed process for producing para-xylene from a feed stream comprising a mixture of $C_8$ aromatic isomers and heavies comprises: feeding first and second feed streams to a xylene fractionation zone to produce a xylenes enriched stream and first bottoms stream; cooling the xylenes enriched stream in a first heat exchanger by transferring heat from the xylenes enriched stream to a first raffinate stream; further cooling the xylenes enriched stream to a temperature in the range of from about 150 to about 170° C. in a second heat exchanger by transferring heat from the xylenes enriched stream to a deheptanizer feet stream; feeding the xylenes enriched stream and a combined desorbent stream to a para-xylene separation zone to produce a first para-xylene enriched stream and the first raffinate stream from the xylenes enriched stream and combined desorbent stream; heating the first para-xylene enriched stream in a third heat exchanger by transferring heat from the combined desorbent stream to the first para-xylene enriched stream and feeding the heated first para-xylene enriched stream into a distillation column to produce a second para-xylene enriched stream and a first desorbent stream; feeding the first raffinate stream, after it has been heated in the first heat exchanger, to a raffinate column to produce a second desorbent stream and a second raffinate stream; combining the first and second desorbent streams to produce the combined desorbent steam; heating the second raffinate stream in a fourth heat exchanger by transferring heat from an isomerization effluent stream to the second raffinate stream and feeding the heated second raffinate stream into an isomerization reactor that converts the second raffinate stream to the isomerization effluent stream; cooling the isomerization effluent stream in the fourth heat exchanger before feeding the cooled isomerization effluent stream to an effluent separator to produce an effluent recycle stream and the deheptanizer feed stream; combining the effluent recycle stream and second raffinate stream upstream of the fourth heat exchanger; heating the deheptanizer feed stream in a fifth heat exchanger by transferring heat from a para-xylene product stream to the deheptanizer feed stream, further heating the deheptanizer feed stream in the second heat exchanger by transferring heat from the xylenes enriched stream to the deheptanizer feed stream and still further heating the deheptanizer feed stream in a sixth heat exchanger by transferring heat from the combined desorbent stream to the deheptanizer feed stream; feeding the deheptanizer feed stream to a deheptanizer column to produce a light overhead stream and the second feed stream; heating the second para-xylene enriched stream in a seventh heat exchanger by transferring heat from the para-xylene product stream to the second para-xylene enriched stream; feeding the second para-xylene enriched stream to a finishing column to produce the para-xylene product stream and a toluene enriched stream.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

By way of example, the example provided in FIGS. 1-8B is directed toward a SMB adsorption-isomerization process loop. Needless to say, the concepts of this disclosure are also applicable to process loops other those disclosed in the Figures. It will be also noted that the order in which process steps are recited is not important unless a process directly depends upon a preceding step or as otherwise indicated.

The simulated moving bed (SMB) adsorptive separation method for the recovery of para-xylene from mixed xylenes and ethylbenzene. The term "mixed xylenes" refers to a mixture of $C_8$ aromatic isomers that includes ethylbenzene, para-xylene, meta-xylene, and ortho-xylene. As shown above in Table 1, these isomers have boiling points so close together that separating them by conventional distillation is not practical. The SMB adsorption separation process provides an efficient means of recovering para-xylene using a solid zeolitic adsorbent that is selective for para-xylene. Currently available SMB adsorption units are designed to recover over 97 wt % of the para-xylene from the feed in a single pass while delivering para-xylene product purity of 99.9 weight % or better The adsorption section of a currently available SMB adsorption unit operates at 177° C. (350° F.) Surprisingly, recent experimental work with a currently employed adsorbent indicates that operating the adsorption section at lower temperatures improves the para-xylene productivity; specifically, for a constant cycle time, adsorbent capacity increases as the adsorption temperature decreases below 177° C. with one preferred adsorption temperature being about 156° C. (313° F.). Of course, the absorption temperature is dependent upon numerous operating variables and can range from about 121° C. (250° F.) to about 204° C. (400° F.), with a more preferred temperature in the range of from about 149° C. (300° F.) to about 177° C. (350° F.).

This disclosure provides for greater productivity from a SMB adsorption unit by providing a means for modifying the absorbent temperature resulting in a capacity increase of about 5% by optimizing the adsorbent temperature for a given set of operating conditions. Thus, this disclosure enables operators to optimize their adsorbent temperature utilizing the heat exchange networks and techniques disclosed herein.

In one example, reducing the adsorption section operating temperature below 177° C. directly impacts the design of the unit (i.e. the adsorbent chamber and the extract and raffinate fractionators), and heat integration with other units in the aromatic complex. Increasing, the area of affected heat exchangers in the conventional heat integration scheme is neither economic nor feasible due to diminishing temperature driving force. Specifically, the potential economic benefit of low temperature operation would be reduced or entirely eliminated due to a combination of excessive capital cost, additional heat exchange surface area and new process/utility exchangers, and operating cost, (i.e. additional hot and cold utility). For example, the conventional 177° C. unit includes heat exchange between desorbent and finishing column reboiler supply in order to cool the desorbent stream down to the adsorption chamber operating temperature. As the operating temperature is reduced below 177° C., the temperature driving force for heat exchange decreases and approaches zero (i.e. infinite surface area exchanger) as the desorbent target temperature approaches the finishing column reboiler supply temperature. Other similarly affected heat exchangers in the unit heat recovery network include the adsorption unit-isomerization liquid, adsorption unit column feed-bottoms and the raffinate column feed-bottoms.

A xylene fractionation, isomerization reactor, and low temperature adsorption unit heat exchange network that maximizes the potential economic benefit associated with operating the adsorption section below 177° C. is disclosed.

Figure 1:
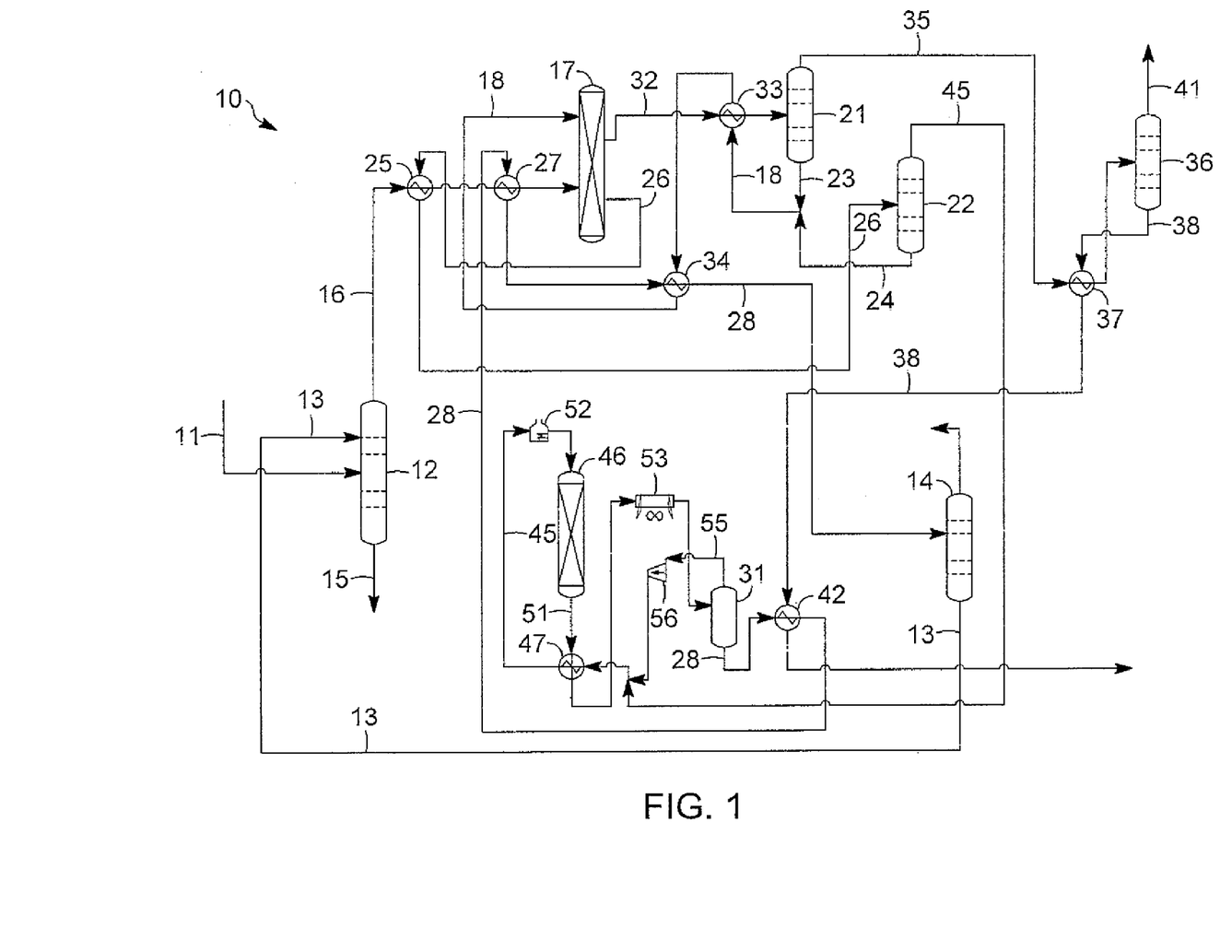
FIG. 1 is a schematic block flow diagram of an aromatics complex designed in accordance with this disclosure.

Turning to FIG. 1, an aromatics complex 10 is illustrated that can receive one or more feed streams shown schematically in the line 11. The feed stream may include any reformate splitter bottoms from a reformate complex (not shown) that generates aromatics from a naptha feedstock. The feed stream may 11 also include a toluene column (not shown) bottoms stream as well. Typically, the feed stream will be treated in a conventional clay treater unit (also not shown in FIG. 1). In any event, the feedline 11 delivers a mixed xylenes feed that may include ethylbenzene to a xylene splitter column 12. The xylene splitter column 12 also receives a second feed stream through the line 13 that constitutes the bottoms stream from the deheptanizer column 14.

Returning to the xylene column 12, a bottom stream is produced through the line 15 which is then delivered to a heavy aromatics column (not shown). Thus, the xylene splitter or separation column 12 removes any remaining $C_9^+$ materials from the first and second feed streams 11, 13 through the bottoms line 15 of the xylene column 12. In an embodiment, the entire xylene column bottoms stream 15 is sent to a transalkylation unit. The overhead stream 16 from the xylene column 12 constitutes a xylenes enriched stream 16 that constitutes the xylene isomers, ethyl benzene and low levels of $C_9$ alkyl aromatics. The xylenes enriched stream 16 is one of the feeds for the para-xylene separation zone 17, the other feed being a combined desorbent stream that passes through the line 18. The recycled desorbent stream 18 comprises desorbent separated as a bottoms product from the para-xylene distillation zone or column 21 and the raffinate distillation column 22. Specifically, the bottoms stream 23 of the para-xylene distillation zone 21 is combined with the bottoms stream 24 of the raffinate column 22 and passed through the line 18 which is a combination of the first desorbent stream from the para-xylene distillation zone 21 and a second desorbent stream from the raffinate column 22.

Figure 6A:
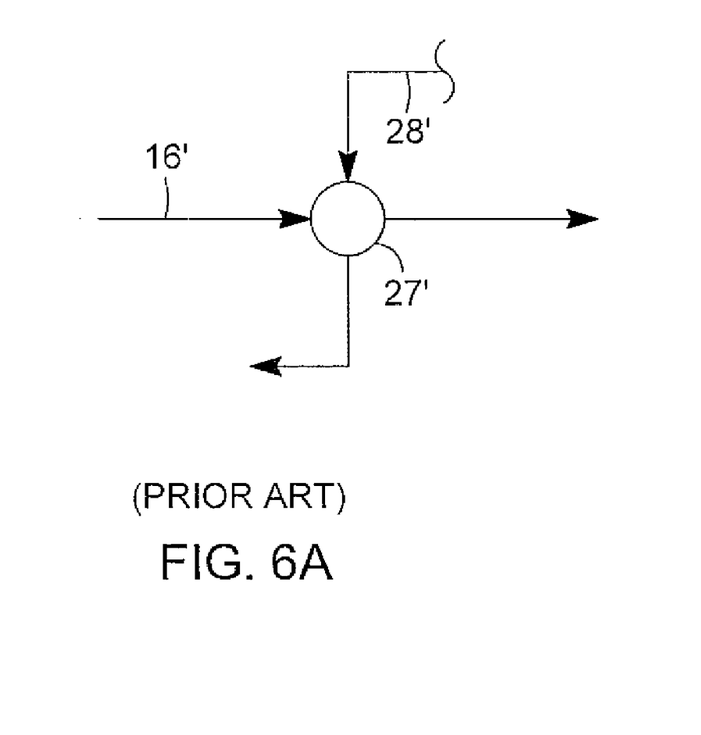
FIG. 6A is a schematic illustration of a conventional heat exchange network used to cool the xylenes enriched stream that is a feed to the para-xylene separation zone to a conventional temperature of about 177° C. (350° F.) by transferring heat from the xylenes enriched stream to the deheptanizer feed stream.
Figure 6B:
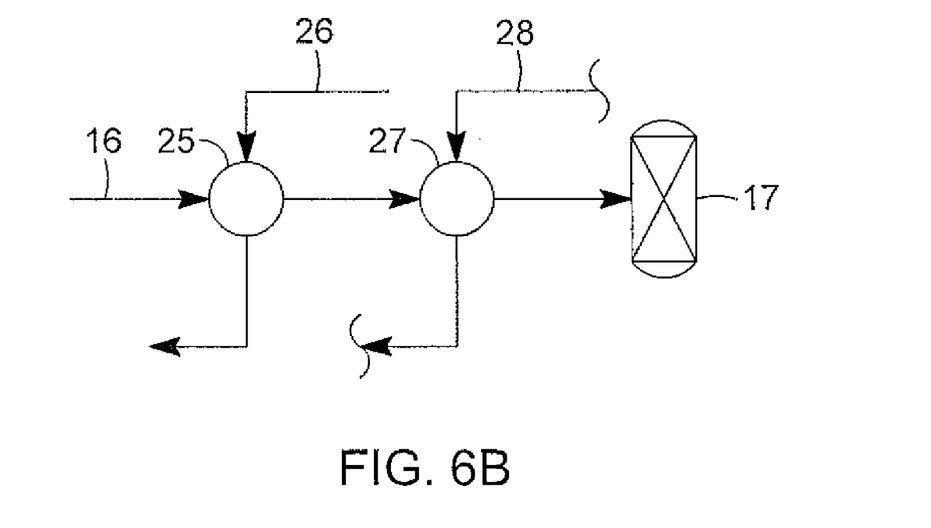
FIG. 6B is a schematic illustration of a disclosed heat exchange network used to cool the xylenes enriched stream that is a feed to the para-xylene separation column to a lower temperature ranging from about 150° C. to about 165° C. by transferring heat from the xylenes enriched stream to the first raffinate stream generated by the para-xylene separation column and also by transferring heat from xylenes enriched stream to the deheptanizer feed stream as illustrated in FIG. 1.

The enriched xylenes stream 16 will exit the xylene column 12 at a temperature that is higher than desirable for the adsorptive separation process carried out in the para-xylene separation zone 17. The reader will note that the disclosed process operates a substantially lower adsorptive separation temperature (156° C. v 177° C.) thereby requiring additional cooling of the enriched xylenes stream 16. This disclosure provides an economical means for cooling the enriched xylenes stream 16 or the feed stream for the para-xylene separation zone 17 to a lower temperature in the range of from about 121° C. to about 204° C. as compared to the conventional temperature of 177° C. (350° F.). Specifically, the xylenes enriched stream 16 is passed through a first heat exchanger 25 that transfers heat from the xylenes enriched stream 16 to the raffinate stream 26 taken off of the para-xylene separation zone 17 as shown in FIGS. 1 and 6B. Then, the xylenes enriched stream 16 is cooled again in a second heat exchanger 27 by transferring heat from the xylenes enriched stream 16 to a deheptanizer feed stream 28 that is generated by the effluent separator 31. The para-xylene separation zone 17 generates a first para-xylene enriched stream 32 and the raffinate stream 26 from the xylenes enriched stream 16 and combined desorbent recycle stream 18. The separator 17, using a plurality of absorbent chambers divided into a number of absorbent beds that are supported by specialized grids or internals for efficient flow distribution. Typically, the separation zone 17 will include about 24 beds with about 26 sets of chamber internals. The para-xylene separation zone 17 may also include to absorbent chambers in series.

Figure 3A:
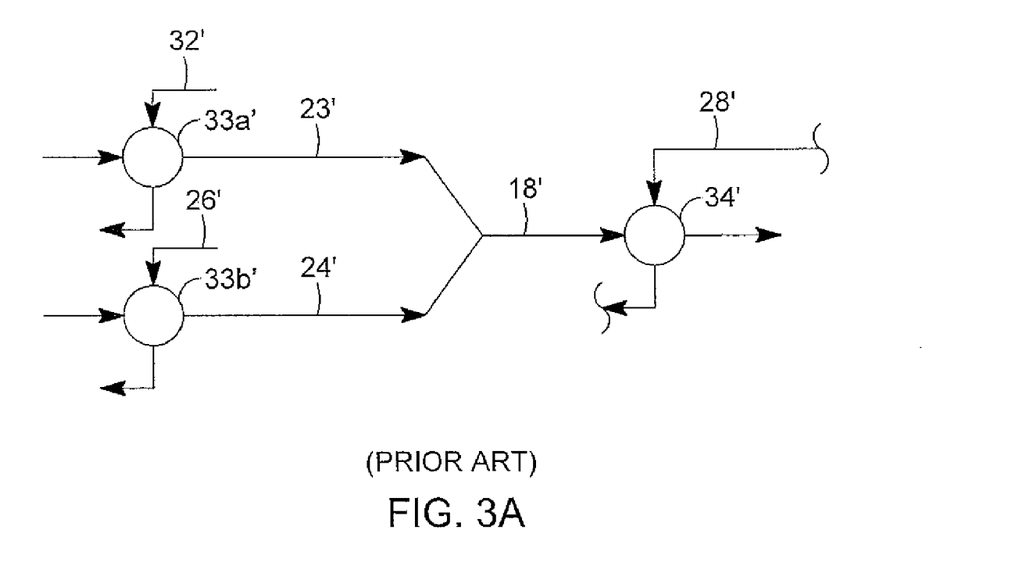
FIG. 3A is a schematic illustration of a conventional heat exchange network used to cool a desorbent stream generated at the bottom of a para-xylene distillation column as well as to cool a desorbent stream generated at the bottom of the raffinate column that treats raffinate generated by the para-xylene separation zone as well as to cool a combined desorbent stream by transferring heat from the combined desorbent stream to a reboiler of a para-xylene finishing column.
Figure 3B:
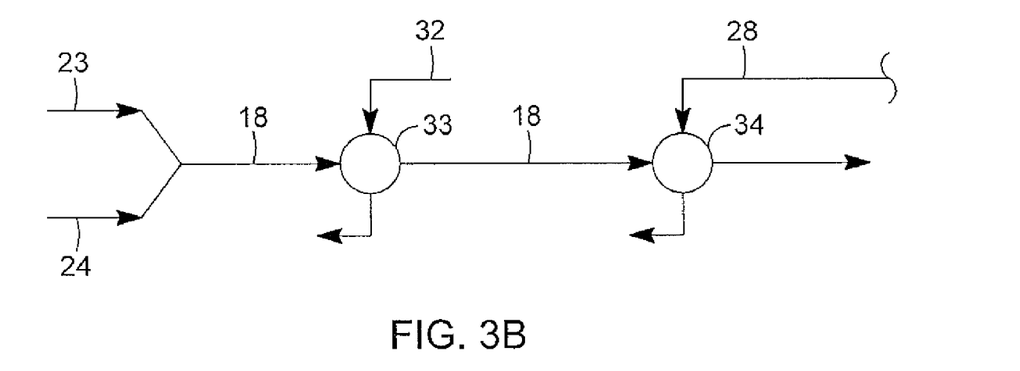
FIG. 3B is a schematic illustration of a disclosed heat exchange network used to cool a combined desorbent stream generated at the bottom of the distillation column and at the bottom of the raffinate column that treats raffinate generated by the low temperature para-xylene separation zone by transferring heat from the combined desorbent stream to the first para-xylene enriched stream that is a product of the para-xylene separation zone and by transferring heat from the combined desorbent stream to a deheptanizer feed stream for a deheptanizer column that is a product of an isomerization effluent separator as shown in FIG. 1.
Figure 7A:
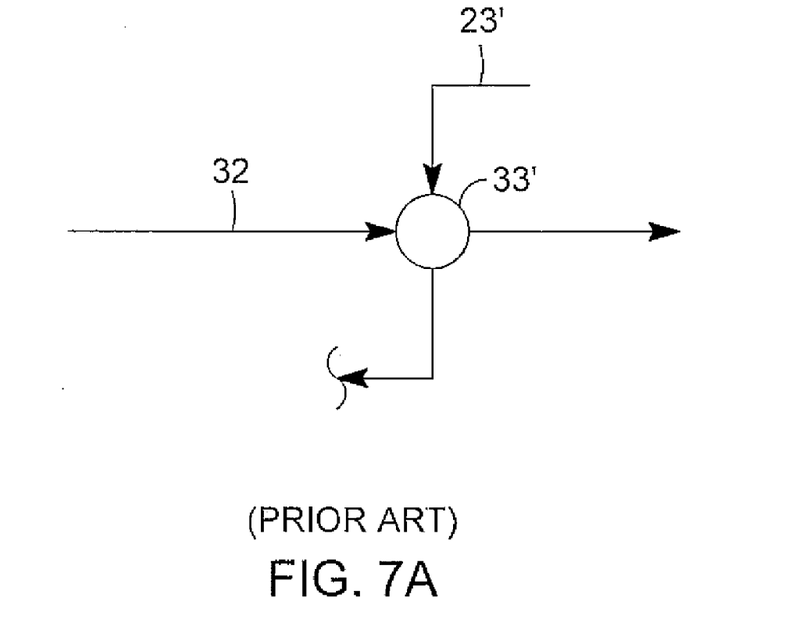
FIG. 7A is a schematic illustration of a conventional heat exchange network used to heat the para-xylene enriched stream generated by the para-xylene separation zone before said stream is introduced to the para-xylene distillation column by transferring heat from the para-xylene distillation column bottom desorbent stream to the para-xylene enriched stream.
Figure 7B:
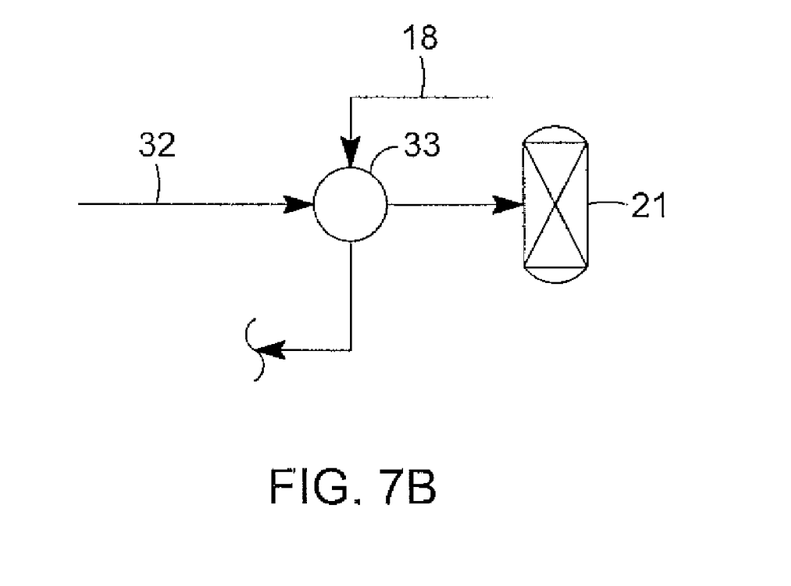
FIG. 7B is a schematic illustration of a disclosed heat exchange network used to heat the first para-xylene enriched stream generated by the para-xylene separation zone before said stream is introduced to the distillation column by transferring heat from a combined desorbent stream as illustrated in FIG. 1.
Figure 8A:
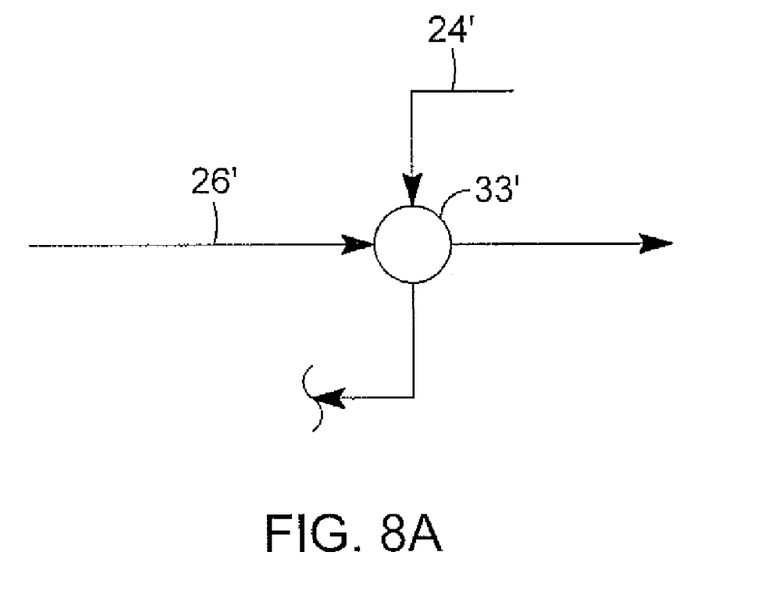
FIG. 8A is a schematic illustration of a conventional heat exchange network used to heat the raffinate stream generated by the para-xylene separation zone before said stream is introduced to the raffinate column by transferring heat from the distillation column bottom desorbent stream to the raffinate stream.
Figure 8B:
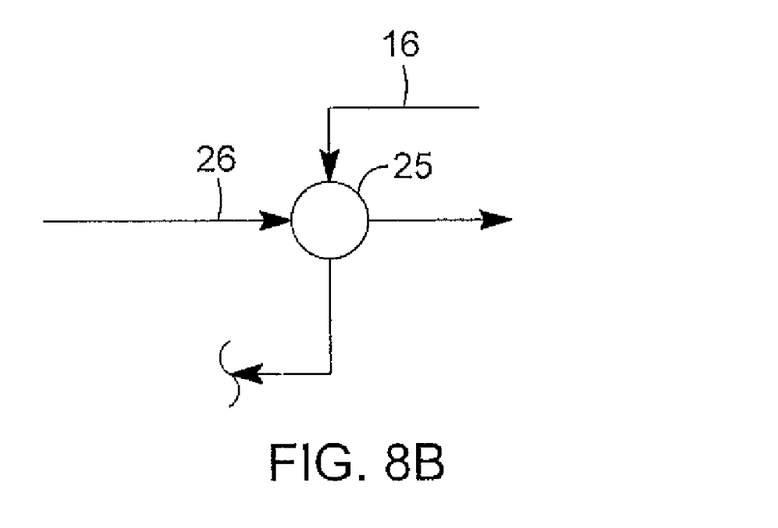
FIG. 8B is a schematic illustration of a disclosed heat exchange network used to heat the first raffinate stream generated by the para-xylene separation zone before said stream is introduced to the raffinate column by transferring heat from the xylenes enriched stream that is the feed to the para-xylene separation column as illustrated in FIG. 1.

Prior to entering the para-xylene distillation zone 21, the first para-xylene enriched stream 32 is heated while the combined desorbent feed 18 is cooled in the heat exchanger 33 (see also FIGS. 3B and 7B). As noted above with respect to the xylenes enriched feed stream 16, the combined desorbent stream 18 must also be cooled to the lower operating temperature of the para-xylene separation zone 17, or from about 121° C. to about 204° C. as compared to the conventional temperature of 177° C. (350° F.). To achieve the lower desorbent stream 18 temperature, a combined desorbent stream 18 is further cooled in the heat exchanger 34 (see also FIG. 3B) which transfers heat from the combined desorbent stream 18 to the deheptanizer feed stream 28 which is then introduced to the deheptanizer column 14.

Figure 4A:
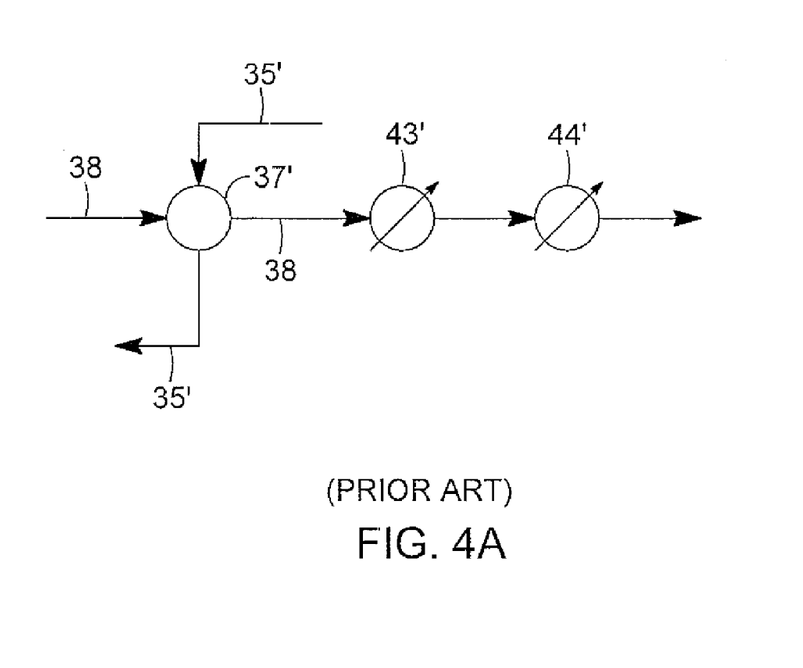
FIG. 4A is a schematic illustration of a conventional heat exchange network used to heat a para-xylene enriched stream that will serve as a feed for a para-xylene finishing column by transferring heat from the para-xylene finishing column bottoms stream to the para-xylene enriched stream.
Figure 4B:
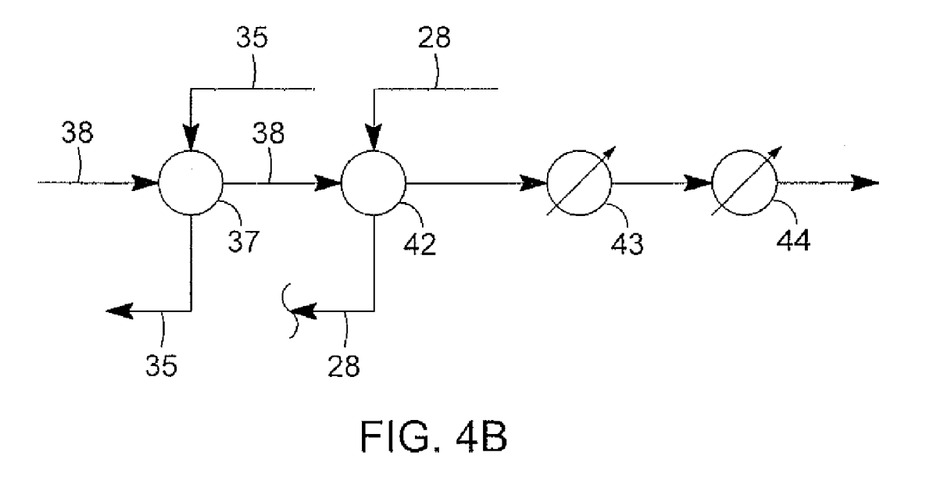
FIG. 4B is a schematic illustration of a disclosed heat exchange network used to heat the second para-xylene enriched stream taken off from the para-xylene distillation column that will serve as a feed for a para-xylene finishing column by transferring heat from the para-xylene product stream generated at the bottom of the finishing column to the second para-xylene enriched stream as shown in FIG. 1.

Following the path of the first para-xylene enriched stream 32, the para-xylene distillation zone 21 removes desorbent from the stream 32 and generates a second, higher concentrated para-xylene stream 35 or para-xylene extract stream, which is then sent to the para-xylene finishing column 36. Prior to be introduced into the para-xylene finishing column 36, the concentrated para-xylene enriched stream 35 is heated in the heat exchanger 37 by transferring heat from the para-xylene product stream 38 to the concentrated para-xylene stream 35 (see also FIG. 4B) The para-xylene product stream 38 is a bottoms product of the finishing column 36. A lighter overhead stream 41 includes residual toluene which can be used as a feed for a transalkylation process (not shown). The para-xylene product stream 38 is also used to heat the deheptanizer feed stream 28 in a heat exchanger 42 as seen in FIGS. 1 and 4B. As seen in FIG. 4B, the para-xylene product stream 38 may be cooled further using air or water coolers shown at 43, 44.

Additional para-xylene may be recovered from the first raffinate stream 26 which serves as the feed for the raffinate column 22 where the desorbent is separated by way of the bottoms stream 24 with a second raffinate stream 45 being taken off the raffinate column 22 as an overhead product. The second raffinate stream 45, in combination with an effluent recycles stream 55, serves as a feed for the isomerization reactor 46. Prior to be introduced into the isomerization reactor 46, the second raffinate stream 45 is heated in the heat exchanger 47 by the transfer of heat from the isomerization reactor product stream 51. The second raffinate stream will typically need to be heated again in a boiler or other heating unit shown at 52 in FIGS. 1 and 2B. In contrast, the isomerization reactor product stream 51 will most likely need additional cooling by way of the air and/or water coolers shown generally at 53, 54 in FIGS. 1 and 2B.

The isomerization reactor product stream 51, after it is been cooled in the heat exchanger 47 and one or more coolers 53, 54, serves as a feed to the effluent separator 31 which removes excess effluent in the form of a recycle stream 55 which passes through a compressor 56 before it is combined with the second raffinate stream 45 as shown in FIG. 1. The isomerization reactor 46 is used to reestablish an equilibrium value of para-xylene in the para-xylene depleted raffinate stream 45. Thus, in the isomerization reactor 46, at least some of the meta-xylene and ortho-xylene are converted to para-xylene. Further, depending upon the catalysts used, residual ethylbenzene can be converted into additional xylenes and/or benzene if a dealkylation catalyst is employed.

The product stream 28 from the effluent separator 31 becomes the feed for the deheptanizer 14. As noted above, the deheptanizer feed 28 can be heated three times—in the heat exchange or 42 which provides heat from the para-xylene product stream 38, the heat exchanger 27 which provides heat from the xylenes enriched stream 16 and the heat exchanger 34 which provides heat from the combined desorbent stream 18.

Figure 2A:
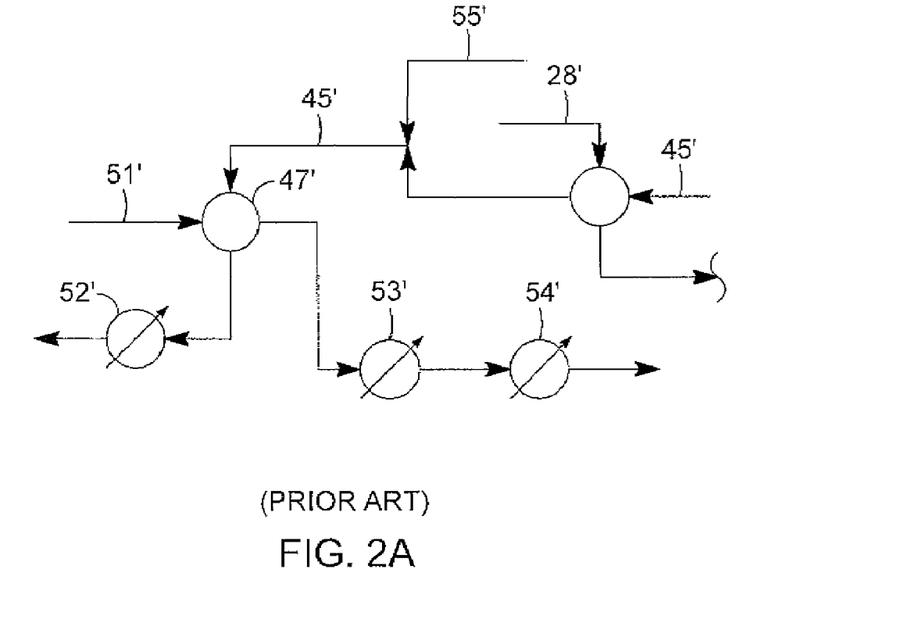
FIG. 2A is a schematic illustration of a conventional heat exchange network used to cool an isomerization reactor product stream by transferring heat from the isomerization reactor product stream to a raffinate stream that is a product of a raffinate column that treats raffinate from a para-xylene separation zone (absorption chamber)
Figure 2B:
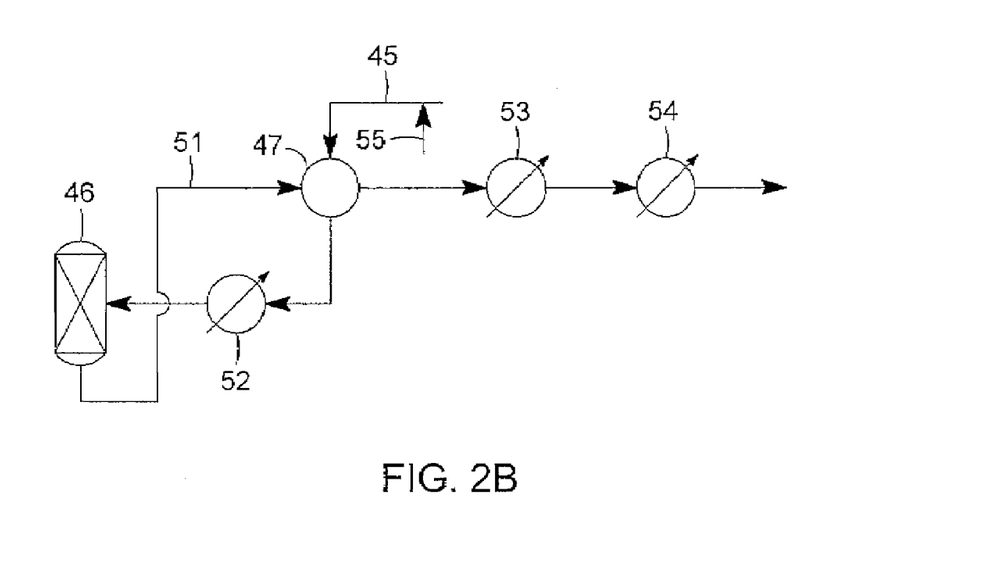
FIG. 2B is a schematic illustration of a disclosed heat exchange network used to cool the isomerization reactor product stream by transferring heat from the isomerization reactor product stream to the raffinate stream that is a product of the raffinate column that treats raffinate from a para-xylene separation zone (absorption chamber) as shown in FIG. 1.

Returning now to FIG. 2B, the heat exchanger 47 is illustrated which cools the isomerization reactor product stream 51' and heats the second raffinate stream 45' which is the feed for the isomerization reactor 46. Referring to FIG. 2A, the conventional design cools the isomerization reactor product stream 51' with the second raffinate stream 45' but the second raffinate stream 45 arrives at the heat exchanger 47' in a heat-depleted state as the second raffinate stream 45' is used to heat the deheptanizer feed 28' Thus, the present disclosure uses the combined desorbent stream 18, the xylenes enriched stream 16 and the para-xylene product stream 38 as heat sources for the deheptanizer feed 28 by way of the heat exchangers 34, 27 and 42 is shown in FIG. 1.

Turning to FIG. 3B, the cooling of the combined desorbent stream 18 is illustrated with the heat exchangers 33 and 34 which transfer heat to the first para-xylene enriched stream 32 and the deheptanizer feed 28 respectively. In contrast, as shown in FIG. 3A, the desorbent streams 23' and 24' are cooled separately, thereby requiring two separate exchangers 33a' and 33b' for heating the first para-xylene enriched stream 32 and first raffinate stream 26' respectively. By heating the raffinate stream 26 with the xylenes enriched stream 16 by way of the exchanger 25, the additional exchanger 33b' is rendered unnecessary. The combined desorbent prior art stream 18' still requires an additional cooling treatment by way of the exchanger 34' that transfers heat to the deheptanizer feed 28' or possibly a finishing column reboiler line.

Turning to FIG. 4B the cooling of the para-xylene product stream 38 is illustrated as the product stream 38 is used in a heat exchanger 37 to heat the second para-xylene enriched stream 35 prior to its introduction into the finishing column 36 and further to heat the deheptanizer feed stream 28 in the exchanger 42. This network is deemed more efficient than the network shown in FIG. 4A which includes only a single exchanger 37' thereby putting a heavier burden on the air cooler 43' and water cooler 44'.

Figure 5A:
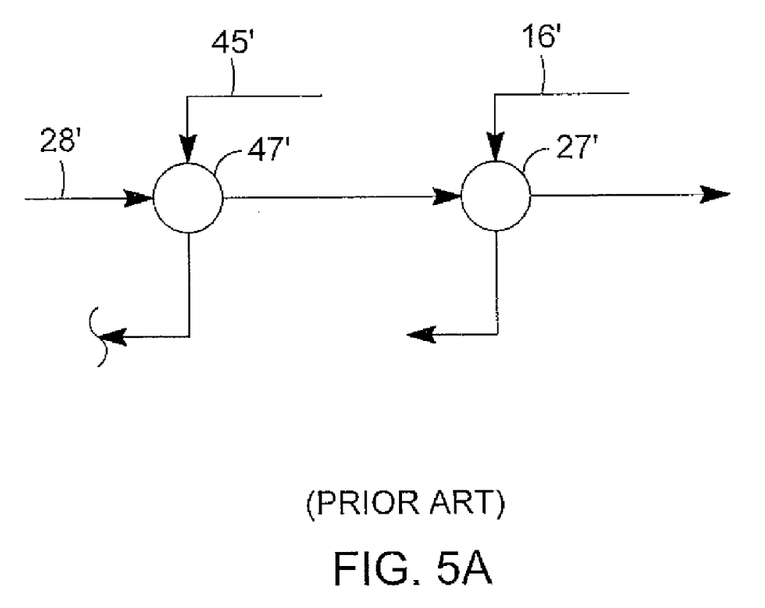
FIG. 5A is a schematic illustration of a conventional heat exchange network used to heat a feed stream for a deheptanizer by transferring heat from the raffinate stream generated by the raffinate column and by transferring heat from the xylenes enriched feed stream that serves as a feed to the para-xylene separation zone.
Figure 5B:
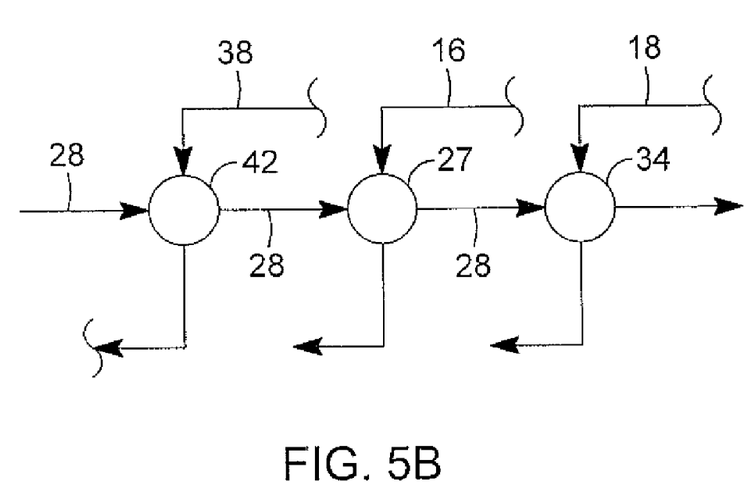
FIG. 5B is a schematic illustration of a disclosed heat exchange network used to heat the deheptanizer feed by transferring heat from the para-xylene product stream to the deheptanizer feed, by transferring heat from the xylenes enriched stream to the deheptanizer feed and by transferring heat from the combined desorbent stream to the deheptanizer feed as illustrated in FIG. 1.

Turning to FIG. 5B, the heating of the deheptanizer feed stream 28 is illustrated using the heat exchangers 42, 27 and 34. In the conventional configuration shown in FIG. 5A, the deheptanizer feed 28' is heated twice using the second raffinate stream 45' and the xylenes enriched stream 16' (or the adsorptive separation feed) as heat sources.

Turning to FIG. 6B, the cooling of the xylenes enriched stream 16 (adsorptive separation feed) is illustrated using the first raffinate stream 26 and the deheptanizer feed 28 as cooling sources. In a conventional system shown in FIG. 6A, only the deheptanizer feed 28' is used as a cooling source with two or more exchangers 27' in series. This approach would not provide the required temperature drop needed to get the xylenes enriched stream 16 down to the preferred operating temperature (150-165° C.) for the separator zone 17.

Turning to FIG. 7B, a heating of the first para-xylene enriched stream 32 is illustrated using the combined desorbent stream 18 is a heat source. In a conventional design shown in FIG. 7A, only the para-xylene distillation column bottoms stream 23' or an uncombined desorbent stream is used to heat the extract column feed 32' as the feed stream 32' is already at a higher operating temperature for the separation column 17' (177° C.). Thus, the design of FIG. 7A would not provide the required increase from the lower separation zone 17 operating temperature (150-165° C.) to the required feed temperature for the para-xylene distillation column 21 which approaches 190° C.

Turning to FIG. 5B, the pre-heating of the first raffinate stream 26 using the exchanger 25 and the xylenes enriched stream 16 as a heat source is illustrated. In contrast, the conventional design shown in FIG. 8A heats the raffinate feed stream 26' using the raffinate bottoms stream 24', which would not provide the required temperature increase for the new raffinate stream 26 (FIG. 8B) which would need to be heated from an operating temperature ranging from about 150 to about 165° C. to a temperature approaching 190° C.

While only certain embodiments have been set forth, alternatives and modifications will be apparent from the above description to those skilled in the art. These and other alternatives are considered equivalents and within the spirit and scope of this disclosure and the appended claims.

What is claimed:

1. A process for producing para-xylene from a feed stream comprising a mixture of $C_8$ aromatic isomers and heavies, the method comprising:
   a) introducing a feed stream to a xylene fractionation zone to produce a xylenes enriched stream;
   b) cooling the xylenes enriched stream by transferring heat from the xylenes enriched stream to one or more of a first raffinate stream and an isomerization reactor product stream;
   c) introducing the xylenes enriched stream and a desorbent stream to a para-xylene separation zone and producing a first para-xylene enriched stream and the first raffinate stream from the xylenes enriched stream and desorbent stream;
   d) heating the first para-xylene enriched stream by transferring heat from the desorbent stream to the first para-xylene enriched stream and feeding the heated first para-xylene enriched stream into a distillation zone to produce a second para-xylene enriched stream and part of the desorbent stream;
   e) introducing the first raffinate stream to a raffinate column to produce another part of the desorbent stream and a second raffinate stream;
   f) heating the second raffinate stream by transferring heat from the isomerization reactor product stream to the second raffinate stream and feeding the heated second raffinate stream into an isomerization zone that converts the second raffinate stream to the isomerization reactor product stream;
   g) heating at least a portion of the isomerization reactor product stream by transferring heat from one or more of a para-xylene product stream, the xylenes enriched stream and the desorbent stream, to the isomerization reactor product stream;
   h) heating the second para-xylene enriched stream by transferring heat from the para-xylene product stream to the second para-xylene enriched stream;
   i) feeding the second para-xylene enriched stream to a finishing column to produce the para-xylene product stream.

2. The method of claim 1, further comprising
   feeding the isomerization reactor product stream to a deheptanizer column to produce a light overhead stream and a second feed stream;
   feeding the second feed stream to the xylene separation zone with the feed stream.

3. The method of claim 2, further comprising
   combining the part of the desorbent stream from the raffinate column and the part of the desorbent stream from the distillation zone to produce the desorbent stream; and
   wherein the isomerization reactor product stream is heated prior to being fed to the deheptanizer column by transferring heat to the isomerization reactor product stream from the desorbent stream.

4. The method of claim 3, wherein the isomerization reactor product stream is also heated by transferring heat from the para-xylene product stream and the xylenes enriched stream to the isomerization reactor product stream.

5. The method of claim 1, wherein the transfer of heat from the xylenes enriched stream to the first raffinate stream of part (b) is carried out in a first heat exchanger.

6. The method of claim 5, wherein the transfer of heat from the xylenes enriched stream to the deheptanizer stream of part (b) is carried out in a second heat exchanger.

7. The method of claim 6, wherein the transfer of heat from the desorbent stream to the first para-xylene enriched stream of part (d) is carried out in a third heat exchanger.

8. The method of claim 7, wherein the transfer heat from the isomerization reactor product stream to the second raffinate stream of part (f) is carried out in a fourth heat exchanger.

9. The method of claim 1, wherein the heating of the isomerization reactor product stream by transferring heat from the para-xylene product stream to the isomerization reactor product stream of part (g) is carried out in a fifth heat exchanger.

10. The method of claim 9, wherein the heating of the isomerization reactor product stream by transferring heat from the desorbent stream to the isomerization reactor product stream of part (g) is carried out in a sixth heat exchanger.

11. The method of claim 10, wherein the heating of the second para-xylene enriched stream by transferring heat from the para-xylene product stream to the second para-xylene enriched stream of part (h) is carried out in a seventh heat exchanger.

12. The method of claim 1 wherein the xylenes enriched stream is cooled in part (b) to a temperature ranging from about 121° C. to about 204° C. prior to being introduced to the para-xylene separation zone in part (c).

13. The method of claim 1 wherein the feed comprises a reformate splitter bottoms stream.

14. The method of claim 1 wherein the feed comprises a combination of a reformate splitter bottoms stream and a toluene column bottoms stream.

15. The method of claim 14 wherein the reformate splitter bottoms stream and toluene column bottoms stream have each been passed through a clay treater prior to being introduced to the xylene fractionation zone.

16. The method of claim 1 further comprising
passing the second raffinate stream through a heater prior to feeding the second raffinate stream to an isomerization zone.

17. The method of claim 1 further comprising
passing the isomerization reactor product stream through a cooler prior to feeding the isomerization reactor product stream to an effluent separator that produces an effluent recycle stream and a deheptanizer feed stream.

18. A process for producing para-xylene from a feed stream comprising a mixture of $C_8$ aromatic isomers and heavies, the method comprising:
introducing a first feed stream to a xylene fractionation zone to produce a xylenes enriched stream;
cooling the xylenes enriched stream to a temperature of between about 155° C. and about 182° C. in a first heat exchanger by transferring heat from the xylenes enriched stream to a raffinate stream and further cooling the xylenes enriched stream in a second heat exchanger by transferring heat from the xylenes enriched stream to a cooled isomerization reactor product stream;
feeding the xylenes enriched stream and a desorbent stream to a para-xylene separation zone to produce a first para-xylene enriched stream and the raffinate stream from the xylenes enriched stream and desorbent stream;
heating the first para-xylene enriched stream in a third heat exchanger by transferring heat from the desorbent stream to the first para-xylene enriched stream and feeding the heated first para-xylene enriched stream to a distillation column to produce a second para-xylene enriched stream;
heating the raffinate stream in a fourth heat exchanger by transferring heat from an isomerization effluent stream to the second raffinate stream and feeding the heated raffinate stream to an isomerization reactor that converts the raffinate stream to the isomerization reactor product stream;
cooling the isomerization reactor product stream in the fourth heat exchanger before heating at least a portion of the isomerization reactor product stream in a fifth heat exchanger by transferring heat from a para-xylene product stream to the isomerization reactor product stream, further heating at least a portion of the isomerization reactor, product stream in the second heat exchanger by transferring heat from the xylenes enriched stream to the isomerization reactor product stream and still further heating at least a portion of the isomerization reactor product stream in a sixth heat exchanger by transferring heat from the desorbent stream to the isomerization reactor product stream;
heating the second para-xylene enriched stream in a seventh heat exchanger by transferring heat from the para-xylene product stream to the second para-xylene enriched stream;
feeding the second para-xylene enriched stream to a finishing column to produce the para-xylene product stream.

19. The method of claim 18 the xylenes enriched stream is cooled to a temperature ranging from about 150° C. to about 170° C. prior to being fed to the para-xylene separation zone.

20. A process for producing para-xylene from a feed stream comprising a mixture of $C_8$ aromatic isomers and heavies, the method comprising:
feeding first and second feed streams to a xylene fractionation zone to produce a xylenes enriched stream and first bottoms stream;
cooling the xylenes enriched stream in a first heat exchanger by transferring heat from the xylenes enriched stream to a first raffinate stream;
further cooling the xylenes enriched stream to a temperature in the range of from about 150 to about 170° C. in a second heat exchanger by transferring heat from the xylenes enriched stream to a deheptanizer feet stream;
feeding the xylenes enriched stream and a combined desorbent stream to a para-xylene separation zone to produce a first para-xylene enriched stream and the first raffinate stream from the xylenes enriched stream and combined desorbent stream;
heating the first para-xylene enriched stream in a third heat exchanger by transferring heat from the combined desorbent stream to the first para-xylene enriched stream and feeding the heated first para-xylene enriched stream into a distillation column to produce a second para-xylene enriched stream and a first desorbent stream;
feeding the first raffinate stream, after it has been heated in the first heat exchanger, to a raffinate column to produce a second desorbent stream and a second raffinate stream;
combining the first and second desorbent streams to produce the combined desorbent stream;
heating the second raffinate stream in a fourth heat exchanger by transferring heat from an isomerization reaction product stream to the second raffinate stream and feeding the heated second raffinate stream into an isomerization reactor that converts the second raffinate stream to the isomerization reaction product stream;
cooling the isomerization reaction product stream in the fourth heat exchanger before feeding the cooled isomerization reaction product stream to an effluent separator to produce an effluent recycle stream and the deheptanizer feed stream;
combining the effluent recycle stream and second raffinate stream upstream of the fourth heat exchanger;
heating the deheptanizer feed stream in a fifth heat exchanger by transferring heat from a para-xylene product stream to the deheptanizer feed stream, further heating the deheptanizer feed stream in the second heat exchanger by transferring heat from the xylenes enriched stream to the deheptanizer feed stream and still further heating the deheptanizer feed stream in a sixth heat exchanger by transferring heat from the combined desorbent stream to the deheptanizer feed stream;

feeding the deheptanizer feed stream to a deheptanizer column to produce a light overhead stream and the second feed stream;

heating the second para-xylene enriched stream in a seventh heat exchanger by transferring heat from the para-xylene product stream to the second para-xylene enriched stream;

feeding the second para-xylene enriched stream to a finishing column to produce the para-xylene product stream and a toluene enriched stream.

\* \* \* \* \*